(12) United States Patent
Barnikol

(10) Patent No.: US 6,956,025 B2
(45) Date of Patent: Oct. 18, 2005

(54) MAMMALIAN HAEMOGLOBIN COMPATIBLE WITH BLOOD PLASMA, CROSS-LINKED AND CONJUGATED WITH POLYALKYLENE OXIDES AS ARTIFICIAL MEDICAL OXYGEN CARRIERS, PRODUCTION AND USE THEREOF

(75) Inventor: Wolfgang Barnikol, Mainz (DE)

(73) Assignee: Sanguibiotech GmbH, Witten (DE)

( * ) Notice: Subject to any disclaimer, the term of this patent is extended or adjusted under 35 U.S.C. 154(b) by 0 days.

(21) Appl. No.: 10/312,517

(22) PCT Filed: Jun. 2, 2001

(86) PCT No.: PCT/EP01/06322

§ 371 (c)(1),
(2), (4) Date: May 22, 2003

(87) PCT Pub. No.: WO02/00768

PCT Pub. Date: Jan. 3, 2002

(65) Prior Publication Data
US 2004/0014641 A1 Jan. 22, 2004

(30) Foreign Application Priority Data

Jun. 29, 2000 (DE) .......................... 100 31 744

(51) Int. Cl.⁷ .................. A61K 38/42; C07K 14/805
(52) U.S. Cl. .......................... 514/6; 530/385
(58) Field of Search ................ 530/350, 385, 530/410, 813; 514/2, 6, 60, 832, 833, 21, 54; 195/63, 168; 424/450, 529; 523/114; 525/54.1; 510/816

(56) References Cited

U.S. PATENT DOCUMENTS

| | | | |
|---|---|---|---|
| 4,001,200 A | | 1/1977 | Bonsen et al. |
| 4,001,401 A | | 1/1977 | Bonsen et al. |
| 4,179,337 A | | 12/1979 | Davis et al. |
| 4,857,636 A | | 8/1989 | Hsia |
| 5,234,903 A | * | 8/1993 | Nho et al. .................. 530/385 |
| 5,312,808 A | | 5/1994 | Shorr et al. |
| 5,386,014 A | | 1/1995 | Nho et al. |
| 5,439,882 A | | 8/1995 | Feola et al. |
| 5,478,805 A | | 12/1995 | Shorr et al. |

FOREIGN PATENT DOCUMENTS

| | | |
|---|---|---|
| DE | 24 99 885 | of 0000 |
| DE | 0 26 07 706 | of 1976 |
| DE | 24 49 885 | 8/1976 |
| DE | 2616 086 | 3/1977 |
| DE | 30 26 398 A | 3/1981 |
| DE | 30 26 398 | 3/1981 |
| DE | 0 31 30 770 | of 1983 |
| EP | 95 107 280 | of 0000 |
| EP | 95 107 289 | of 0000 |
| EP | 97 100 790 | of 0000 |
| EP | 0 067 029 | 12/1982 |
| EP | 0 067 029 A | 12/1982 |
| EP | 0 069 026 A | 1/1983 |
| EP | 0 201 618 | 11/1986 |
| EP | 0 206 448 A1 | 12/1986 |
| EP | 0 528 841 | 3/1993 |
| EP | 0 854 151 A | 7/1998 |
| EP | 0 854 151 | 7/1998 |
| WO | WO 91/07190 | 5/1991 |

OTHER PUBLICATIONS

Ton T. Hai et al: "Polymerization of Diaspirin Crosslinked Hemoglobin (DCLHb) with PEG Activated with Benzene–sulfonate Bearing Electron–Withdrawing Groups"; Tetrahedron 55 (1999) 2147–2156 XP–002183148.

T.T. Hai et al: "Diaspirin Crosslinked Hemoglobin (DCLHb) Polymerization"; Art. Cells, Blood Subs., And Immob. Biotech., 22(3) 923–931 (1984) XP–001039974.

Fitzgerald, L.R; "Cutaneous Respiration in Man"; Cutaneous Respiration, Division of Anatomy, University of Tennessee Medical Units, Memphis, TN, Jul. 1957, pp. 325–336, vol. 37.

Barnikol, W.K.R.et al; "Die Feinstruker der Sauerstoff–Hämoblogin–Bindung als Hilfsmittel zum Studium pharmakologischer Wirkungen . . . "; Physiologisches Institut der Johannes Guttenberg–Germany, Funkt. Biol. med. 2, (1983), pp. 245–249.

Kothe, N., et al; "Characterization of a modified, stroma–free hemoglovin solution as an oxygen–carrying plasma substitute"; Scientific Department of Biotest Pharma GmbH, Frankfurt, Germany; Surgery, Gynecology & Obstertrics, Dec. 1985, vol. 161, pp. 563–569.

Bosman, R.J. et al. "Free Polymerized Hemoglobin Versus Hydroxyethyl Starch in Resuscitation of Hypovolemic Dogs", Anesth. Analg. 75, pp. 811–817.

Pabst, R.; "Sauerstofftransport mit stromafreien Hämoglobinlösungen und Fluorocarbonen"; Med. Klin. 72 (1977) pp. 1555–1562, vol. 39.

Chang, T.M.S., "How safe are modified hemoglobins?" Blood Substitutes: Present and Future Perspectives, Elsevier Science, Amsterdam (1998).

Keipert, et al, "Pyridoxylated Polyhemoglobin as a red cell substitute for resuscitation of lethal hemorrhagic shock in conscious rats"; Biomat. Med. Dev. Art. Org. 13 (1&2), pp. 1–15 (1935).

(Continued)

Primary Examiner—Robert A. Wax
Assistant Examiner—Robert B. Mondesi
(74) Attorney, Agent, or Firm—Norris McLaughlin & Marcus, P.A.

(57) ABSTRACT

The invention relates to covalently cross-linked mammalian hemoglobins, to which polyalkylene oxides are covalently linked. Such hemoglobins are surprisingly compatible with proteins of human and animal plasma, under all the possible conditions within the vascular system of the body. The invention furthermore relates to the production of these cross-linked hemoglobins linked with polyalkylene oxides, as well as to their use as artificial intravasal oxygen carriers in the human or animal organism or in individual organs.

17 Claims, 6 Drawing Sheets

OTHER PUBLICATIONS

Figure 1:
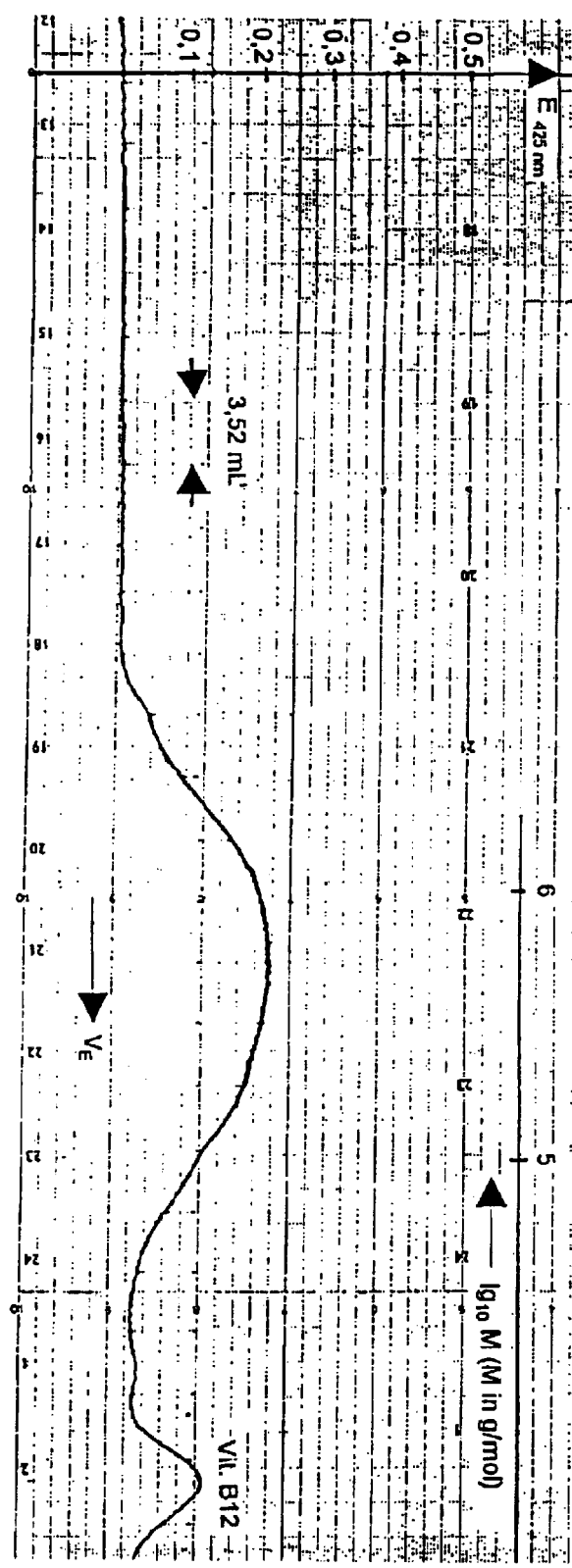

Hirlinger, W.K., et al, "Effects of a Partial Exchange with Fluosol DA 20% on healthy Pig", Anästhesist 31, pp. 660–666 (1982).

Keipert, et al; "Pyridoxylated–polyhemoglobin solution: a low viscosity oxygen–delivering blood replacement fluid with normal oncotic pressure and long–term storage feasibility"; Artificial Cells & Organs Research Centre, Faculty of Medicine, McGill University, Montreal, Canada, pp. 185–197.

Hunt, C.A., et al, "Synthesis and Evaluation of a Protypal Artificial Red Cell", Science, 230: pp. 1165–1168 (1985).

Farmer, M.C.; et al; "Preclinical data and clinical trials with diaspirin cross–linked hemoglobin"; Artificial Red Cells, edited by E. Tsuchida, (1995) John Wiley & Sons pp. 177–185.

Keipert P.E., et al, "Metabolism, Distribution, and Excretion of HbXL: A Nondissociation Interdimerically Crosslinked Hemoglobin with Exceptional Oxygen Offloading Capability", Chang, T.M.S., Geyer R. P. (Eds.): Blood Substitutes, Marcel Dekker, New York (1989).

Chang T.M.S., "Modified Hemoglobin as Red Cell Blood Substitutes", Biomat. Art. Cells, Art. Org. 15(2), pp. 323–328 (1987).

Friedman H.J., et al, "In Vivo Evaluation of Pyridoxylated–Polymerized Hemoglobin Solution", Surg. Gynecol., Obstet.; 159, pp. 429–435 (1984).

Bakker, J.C. et al; "Properties of hemoglobin interdimerically cross–linked with NFPLP"; Biomet. Art. Cells & Immob, Bio., vol. 16, pp. 635–636 (1988).

Barnikol, W.K.R. et al, "Hyperpolymeric Hemoglobins and Artifical Oxygen Carriers. An Innovative Attempt at Medical Development", Therapiewoche 46: pp. 811–815 (1996).

Pötschke, H. et al; "Vernetzte globuläre proteine –eine neue klasse halbsynthetischer makromoleküle: . . . "; Macromol. Chem. Phys. 197, pp. 1419–1437 (1996).

Barnikol, W.K.R., "the Influence of Glutardialdehyde on the Oxygen Cooperativity of Human Hemoglobin", Pflügers Archi 406: R 61 (1986).

Conover et al, "The ability of polyethylene glycol conjugated bovine hemoglobin (PEG–Hb) to adequately deliver oxygen in both exchange transfusion and top–loaded rat models"; Art. Cells, Blood Subst. Immobil. Biotech. 27: pp. 93–107 (1999).

Looker, D, et al; "A human recombinant haemoglobin designed for use as a blood substitute"; Nature. vol. 356, Mar. 19, 1992; pp. 258–260.

Xue, H. et al; "Preparation of conjugated hemoglobins"; Methods in Enzymology, vol. 231, pp. 308–323 (1994).

Barnikol, W.K.R., et al; "Highly polymerized human haemoglobin as an oxygen–carrying blood subsititute", Advances in Experimental Medicine and Biology, vol. 215, pp. 129–134 (1987).

Tam, et al., "Blood replacement in dogs by dextran–hemoglobin"; Can. J. Biochem, vol. 56 (1978); pp. 981–984.

Gould, et al; "The clinical development of human polymerized hemoglobin"; Blood Substitutes: principles, methods, products and clinical trials, edited by Thomas Ming Swi Chang (1998).

Bakker et al.; "Preparation and characterization of crosslinked and polymerized hemoglobin solutions", Biomat., Art. Cells & Immob. Biotec., 20(2–4), pp. 233–241 (1992).

"Points to consider in the safety evaluation of hemoglobin–based oxygen carriers"; Center for Biologies Evaluation and Research; Transfusion vol. 31, 4 (1991) pp. 369–371.

Pötzschke, H. et al "A novel method for determining molecular weights of widely distributed polymers with the help of gel photography and viscosimetry using hemoglobin hyperpolymers as examples", Macromolecular chemistry and Physics 197, pp. 3229–3250 (1996).

Barnikol, W.K.R. et al, "An improved modification of the micro–method according to the measurement of Niesel and Thews for $O_2$–Hb–binding curves in whole blood and concentrated Hb solutions", Respiration 36, pp. 86–95 (1978).

Sharma et al; "Role of no mechanism in cardiovascular effects of diaspirin cross–linked hemoglobin in anesthetized rats"; American Physiological Society; pp. 1379–1388 (1995).

Rohlfs et al; "Arterial blood pressure responses to cell–free hemoglobin solutions and the reaction with nitric oxide"; The Journal of Biological Chemistry, vol. 273, No. 20, Issue of May 15, pp. 12128–12134 (1998).

Rodeberg et al; "Nitric oxide: and overview"; The AmericanJournal of Surgery, vol. 170, Sep. 1995, pp. 292–303.

Vogel, et al; "Coronary constrictor effect of stroma–free hemoglobin solutions"; The American Journal of Physiol., vol. 251; pp, H413–H420 (1986).

Pötzschke, et al; "A new type of artificial oxygen carrier: soluble hyperpolymeric haemoglobin with negligible oncotic pressure –production of thermally stable hyperpolymers from human blood with glutaraldehyde as corss–linker"; Biomat., Art. Cells && Immob, Biotech., 20(2–4), pp. 287–291 (1992).

Pötzschke et al; "Molar masses and structure in solution of haemoglobin hyperpolymers–a common calibration of size exclusion chromatography of these artificial oxygen carriers"; Art. Cells, Blood Subs., and Immob. Biotech., 25(6), pp. 527–540 (1997).

Pearce et al; "Overvies of preclinical and clinical efficacy of biopure's HBOCs"; Blood substitutes: Principles, Methods, Products and Clinical Trials, edited by Thomas Ming Swi Chang (1998) Chapter 5.

Pötzschke, et al; "Divinyl sulfone cross–linked hyperpolymeric human haemoglobin as an artifical oxygen carrier in anaesthetized spontaneously breathing rats"; Oxygen transport to tissue XV, edited by P. Vaupel, et al, Plenum Press, New York (1994) pp. 205–213.

* cited by examiner

MAMMALIAN HAEMOGLOBIN COMPATIBLE WITH BLOOD PLASMA, CROSS-LINKED AND CONJUGATED WITH POLYALKYLENE OXIDES AS ARTIFICIAL MEDICAL OXYGEN CARRIERS, PRODUCTION AND USE THEREOF

This application is a 371 of PCT/EP01/06322, filed on Jun. 2, 2001.

The invention relates to covalently cross-linked mammalian hemoglobins, to which polyalkylene oxides are covalently linked. Such hemoglobins surprisingly are compatible with proteins of human and non-human animal plasma, under all the possible conditions within the vascular system of the body. The invention furthermore relates to the production of these cross-linked hemoglobins linked with polyalkylene oxides, as well as to their use as artificial intravasal oxygen carriers in the human or non-human animal organism, in individual organs, or for biomedical purposes.

Artificial oxygen carriers are substances, which reversibly bind and release oxygen in a manner suitable for an organism, as well as can replace or support the oxygen transport function of the blood. Pharmaceutical formulations of solutions or suspensions of artificial oxygen carriers are being developed in order to be administered parenterally into the circulatory system, particularly intravenously, to humans or animals, for the treatment of acute and chronic oxygen deficiency states as well as acute blood losses. Furthermore, they can also be used for the perfusion of organ transplants or as an additive to cell cultures, in order to improve the oxygen supply here.

Artificial oxygen carriers made from hemoglobins are being developed worldwide, on the basis of different concepts (state of the art: Rudolph, A. S. et al. (Eds.): *Red Blood Cell Substitutes: Basic Principles and Clinical Applications*, Marcel Dekker, New York and others, 1998; Tsuchida, E. (Ed.): *Blood Substitutes: Present and Future Perspectives*, Elsevier Science, Amsterdam 1998; Chang, T. M. S. (author and ed.): *Blood Substitutes: Principles, Methods, Products and Clinical Trials, Volume 1 and ~Volume 2*, Karger Landes, Basel and others, 1997 and 1998). All of the concepts have in common the production of artificial carriers with suitable oxygen binding properties, which can guarantee oxygen transport in vivo. These properties are directed according to the desired area of application of the carrier, and are generally oriented according to the properties of human blood. Untreated, extracellularly dissolved hemoglobin is not suitable as an oxygen carrier, since it decomposes into its sub-units intravasally, and these are rapidly excreted via the kidneys, because of their low molecular weight. For this reason, attempts are being made to extend the intravasal dwell time of natural hemoglobins, or those produced by means of gene technology, in the organism. Extensions of the intravasal dwell time result from microencapsulation of hemoglobin solutions in liposomes, so-called hemosomes (Ogata, Y. (1994): "Characteristics of Neo Red Cells, Their Function and Safety: In Vivo Studies," *Artificial Cells, Blood Substitutes, and Immobilization Technologies* 22: 875-881);

covalent intramolecular links, i.e. stabilization of the quaternary structure of the hemoglobins, by means of bifunctional cross-linking agents (Farmer, M. C., et al. (1995): "Preclinical Data and Clinical Trials with Diasparin Cross-linked Hemoglobin,"—Tsuchida, E. (Ed.): *Artificial Red Cells*, John Wiley, 1995: 177-185; Bakker, J. C., et al. (1988): "Properties of Hemoglobin Interdimerically Cross-linked with NFPLP," *Biomaterials, Artificial Cells, and Immobilization Biotechnologies* 16: 635–636) or from gene technology production (Looker, D., et al. (1992): "A Human Recombinant Haemoglobin Designed for Use as a Blood Substitute," *Nature* 356: 258–260);

covalently linking of macromolecules to the hemoglobin, for example polysaccharides, dextrans, hydroxyethyl starch, insulin, or artificial water-soluble macrocomolecules such as polyethylene glycols (Xue, H., Wong, J. T. -F. (1994): "Preparation of Conjugated Hemoglobins,"—Abelson, J. N., Simon, M. I. (Ed.): *Methods of Enzymology*, Volume 231 B, Academic Press 1994: 308–322; Tam, S. C., et al. (1978): "Blood Replacement in Dogs by Dextran-Hemoglobin," *Canadian Journal of Biochemistry* 56: 981–984; patents DE-A 30 26 398 (1981): "Modifiziertes Hämoglobin enthaltender Blutersatz" (Blood substitute containing modified hemoglobin); EP-A 0 069 026 (1982): "Oxygen Carrier"; EP-A 0 206 448 (1986): "Hemoglobin combined with a Poly (Alkylene Oxide)"; U.S. Pat. No. 5,234,903 (1993): "Chemically Modified Hemoglobin as an Effective, Stable, Non-immunogenic Red Blood Cell Substitute" and U.S. Pat. No. 5,312,808 (1994): "Fractionation of Polyalkylene Oxide-Conjugated Hemoglobin Solutions");

intermolecular cross-linking (polymerization) of the hemoglobins with bifunctional cross-linking agents, (Gould, S. A., et al. (1998): "The Clinical Development of Human Polymerized Hemoglobin,"—Chang, T. M. S. (Ed.): *Blood Substitutes: Principles, Methods, Products and Clinical Trials, Volume* 2, Karger Landes Systems 1998: 82–98; Bakker, J. C., et al. (1992): "Preparation and Characterization of Cross-linked and Polymerized Hemoglobin Solutions," *Biomaterials, Artificial Cells, and Immobilization Biotechnologies* 20: 233–241).

The artificial oxygen carriers last mentioned, based on cross-linked hemoglobins, have a number of advantages over other oxygen carriers: Sufficiently large cross-linked hemoglobins (hemoglobin polymers have such a low colloidal osmotic pressure that they not only can be used as an oxygen-transporting blood volume substitute to replace missing blood, because of their low inherent colloidal osmotic pressure, then in combination with a plasma expander, but particularly can also be added to the blood as an oxygen-transporting blood additive (Barnikol, W. K. R., et al. (1996): "Hyperpolymere Hämoglobine als künstliche Sauerstoffträger. Ein innovativer Ansatz der medizinischen Entwicklung" (Hyperpolymeric hemoglobins as artificial oxygen carriers. An innovative approach of medical development), *Therapiewoche* 46:811–815). Areas, in which the use of such oxygen transport additives is indicated, are the treatment of many chronic oxygen deficiency states, such as, for example, anemia, strokes, or cardiac infarctions. Treatment with such an additive is always possible, even without blood loss, while all the other volume substitutes that transport oxygen are exclusively suitable for treatment of acute oxygen deficiency states after blood losses. Cross-linked hemoglobins with a high degree of cross-linking furthermore possess the advantage of a particularly long intravasal dwell time. Furthermore, after their administration, increases in blood pressure do not have to be expected, since they do not leave the blood vessels, because of their size, and therefore cannot act as constrictors of the blood vessel musculature (see below).

Equivalent to efficacy, the evaluation of, and, if possible, improvement of the safety of artificial oxygen carriers always stands in the center of all development (Fratantoni, J. C. (1991): "Points to Consider in the Safety Evaluation of Hemoglobin-based Oxygen Carriers," *Transfusion* 31: 369–371). For example, an increase in blood pressure and an increase in the total peripheral vascular resistance are observed in anesthetized rats after intravasal administration of intramolecularly cross-linked hemoglobins (Sharma, A. C., et al. (1993): "Role of NO Mechanism in Cardiovascular Effects of Diaspirin Cross-linked Hemoglobin in Anesthetized Rats," *American Journal of Physiology* 269: H 1379–H 1388). This vasoconstrictor effect of molecular-disperse artificial oxygen carriers can be based both on hyperoxygenation of the tissue by means of the very effective carriers (Rohlfs, R. J., et al. (1998): "Arterial Blood Pressure Responses to Cell-free Hemoglobin Solutions and the Reaction with Nitric Oxide," *Journal of Biological Chemistry* 273: 12128–12134), or also on the inhibition of the local effect of the nitrogen monoxide (NO) by means of hemoglobins (Sharma, A. C., et al. (1993)—see above), because nitrogen monoxide has a dilating effect on the smooth muscles of the blood vessel walls (Roderberg, D. A., et al. (1995): "Nitric Oxide: An Overview," *American Journal of Surgery* 170: 292–303). Because of its low molecular weight, hemoglobin leaves the vascular system, binds nitrogen monoxide given off endothelially, and thereby shifts the equilibrium that prevails at the vascular musculature between vasodilatation and vasoconstriction, in the direction towards the latter. Crosslinking of hemoglobin molecules (to multimers: oligomers and polymers) prevents diffusion out of the blood vessels and thereby an increase in blood pressure, by means of the artificial carriers (Vogel, W. M., Valeri, C. R. (1986): "Coronary Constrictor Effect of Stroma-free Hemoglobin Solutions," *American Journal of Physiology* 251: H 413–H 420).

Furthermore, the effect of the artificial carriers on the coagulation system, the immune defense system, particularly complement activation, activation of the reticuloendothelial system, and the specific immune response are of great interest. It was possible to show (Ning, J., Chang, T. M. S. (1990): "Effects of Homologous and Heterologous Stroma-free Hemoglobin and Polyhemoglobin on Complement Activation, Leukocytes and Platelets," *Biomaterials, Artificial Cells, and Artificial Organs* 18: 219–233; Feola, M., Simoni, J. (1991): "Biocompatibility of Hemoglobin Solutions: The Effects of Contaminants, Hemoglobin and Hemoglobin Derivatives," *Biomaterials, Artificial Cells and Artificial Organs* 19: 382) that complement activation is triggered not by untreated or linked hemoglobin itself, but rather essentially by contaminants, for example endotoxins or stromal components of the erythrocytes that contain the untreated hemoglobin, at first. Therefore the use of highly pure starting solutions for the production of artificial oxygen carriers can prevent subsequent complement activation.

Homologous hemoglobins (hemoglobins of the same animal species, to which it is being administered), whether untreated or cross-linked, do not have an immunogenic effect in animal models, even after repeated administration, while heterologous hemoglobins (hemoglobins from a species different from the recipient) or their cross-linking products, on the other hand, can provoke antibody production and an anaphylactic reaction after repeated administration (Chang, T. M. S. (1997): "How Safe are Modified Hemoglobins?", *Blood Substitutes: Principles, Methods, Products and Clinical Trials, Volume* 1, Karger Landes Systems 1997: 49–72). Methods for masking the antigenicity of hemoglobins are microencapsulation or conjugation with polyethylene glycol (e.g. U.S. Pat. No. 4,179,337: "Non-immunogenic Polypeptides."

Within the scope of the study concerning the safety of artificial oxygen carriers, direct interactions of the latter with plasma proteins with which they come into contact during intravasal administration have not been given any attention until now. In our own studies, it was possible to demonstrate, using a new in vitro biocompatibility test, that cross-linked hemoglobins and plasma proteins are compatible with one another to varying degrees, as a function of the pH. What mainly occurs is the precipitation of mostly red or reddish tinged light precipitates, which are generally visually recognizable—less obvious precipitates can be detected using sensitive cloudiness measurements. These precipitates either relate predominantly to either the cross-linked hemoglobins or the plasma proteins, or equally to both. Detection of the involvement of plasma proteins, in other words the presence of interactions between cross-linked hemoglobins and plasma proteins, is possible, if applicable, because a decrease in the content of plasma proteins, particularly the γ-globulins, can also be measured in the top plasma fraction by means of electrophoresis, for example. In this connection, the extent of hemoglobin precipitates is dependent, among other things, on the molecular weight of the cross-linked hemoglobins, on the hemoglobin used, and on the bifunctional cross-linking agent, as well as on the presence of covalently bonded effectors of the oxygen bonding properties of the hemoglobins (Domack, U. (1997): "Entwicklung und in vivo-Evaluation eines künstlichen Sauerstoffträgers auf Basis von Rinderhämoglobin" (Development and in vivo evaluation of an artificial oxygen carrier on the basis of bovine hemoglobin), *Dissertation, Department of Chemistry, Johannes Gutenberg University*, Mainz 1997). For example, greater proportions precipitate out of a cross-linked bovine hemoglobin produced with the bifunctional cross-linking agent glutardialdehyde, with an average degree of cross-linking of about 10, in human plasma, at pH values less than 7.5. Modification of the oxygen bonding properties of cross-linked bovine hemoglobin by means of covalent linking of pyridoxal-5'-phosphate results in a further reduction of the plasma compatibility. In this case, precipitation of the hemoglobin is already observed at pH values below 8.0. Cross-linked bovine hemoglobins modified with pyridoxal-5'-phosphate, produced using glutardialdehyde as the cross-linking agent, are compatible with human plasma only up to a degree of polymerization of about five (hemoglobin oligomers), in the physiologically relevant pH range.

A positive effect on the biocompatibility between cross-linked bovine hemoglobin and human plasma can be achieved, on the other hand, by using bifunctional cross-linking agents that introduce additional solvatizing groups during polymerization. For example, bovine hemoglobin polymers that are soluble in plasma without any precipitation, even at average degrees of polymerization of 24, can be produced using the cross-linking agent 2,5-diisothiocyanatobenzene sulfonic acid. However, these polymers are completely unsuitable for use as artificial oxygen carriers, because of their oxygen binding properties (Domack, U. (1997), see above).

According to the current state of the art, it is not possible to produce crosslinked hemoglobin, particularly with higher degrees of cross-linking, using many bifunctional cross-linking agents, without having to expect incompatibility in the form of precipitation after they are mixed with plasma, under certain conditions. In the case of physiological and pathophysiological pH values, incompatibility between cross-linked hemoglobins and plasma proteins is observed in vitro: Both plasma proteins and cross-linked hemoglobins precipitate; in certain cases, the precipitation of the one or the other can predominate. This is particularly true for highly cross-linked hemoglobins (hemoglobin polymers), less for hemoglobin oligomers that are cross-linked to a lesser degree. It should be expected that such hemoglobin/plasma protein incompatibility will also occur in the vascular system during use in vivo, and, in extreme cases, will result in multiple occlusions of smaller blood vessels.

In order to guarantee the ability of the carriers to function, and to avoid serious side effects when using them in the human or animal organism, for example shock caused by capillary stasis, the cross-linked hemoglobins must be compatible with the blood, particularly the proteins contained in the plasma, specifically both under physiological conditions and under all pathophysiological conditions: This holds true, in particular, also for acidosis, as it occurs locally in tissue that is being insufficiently supplied with oxygen. Such interactions between cross-linked hemoglobins and plasma components must be reliably prevented under all conditions that result in precipitation of a component and are possible in the organism.

The invention is therefore based on the task of producing cross-linked hemoglobins for which it is guaranteed that they are compatible with the plasma proteins after intravasal administration in the organism, even under extremely pathophysiological pH values.

This objective is accomplished, pursuant to the invention, in that polyalkylene oxides with a moderately high molecular weight are covalently bonded to the hemoglobin molecules cross-linked with a cross-linking agent. Polyalkylene oxides covalently linked with the cross-linked hemoglobins to a sufficient degree alone have the result that even under extreme pathophysiological pH value conditions (pH values between 6.8 and 7.4), no incompatibility of cross-linked hemoglobins and plasma proteins can be determined in the form of precipitation of one and/or the other component. This could not be expected, since the problem is completely new and solutions of similar or even analogous problems are not available. Furthermore, a combination of both cross-linking of the hemoglobin and covalent linking of the polyalkylene oxide appears to be superfluous, when viewed in the foreground: Both methods, according to the state of the art, result in the same thing, namely a certain lengthening of the intravasal dwell time of artificial oxygen carriers produced from modified hemoglobin, but the necessary degree of lengthening is already achieved by carrying out one of the methods. On the other hand, it is known that polyalkylenes are effective precipitants for proteins, by means of solvent exclusion. Technical methods for the preparative separation of proteins by means of fractionated precipitation during a consecutive increase of the concentrations of the polyalkylene oxides are based on this. It was all the more surprising that it was possible to solve the problem on which the application is based with the inventive method.

Suitable as hemoglobin starting material for the inventive teachings is monomeric, untreated hemoglobin or hemoglobin linked with certain effectors, e.g. the oxygen affinity of hemoglobin, such as pyridoxal-5'-phosphate or 2-nor-2-formyl-pyridoxal-5'-phosphate, for example (as described in Kothe et al. (1985), *Surgery, Gynecology & Obstetrics* 161: 563–569 or Van Der Plas et al. (1987), *Transfusion* 27: 425–430 and (1988), *Transfusion* 28: 525–530, additional citations in: Rudolph, A. S. et al. (eds).: Red Blood Cell Substitutes: Basic Principles and Clinical Applications, Marcel Dekker, New York and others 1998; Tsuchida, E. (ed.): Blood Substitutes: Present and Future Perspectives, Elsevier Science, Amsterdam 1998, Volume 1 and Volume 2, Karger Landes, Basel and others 1997 and 1998, see also EP 0 528 841, where the pyridoxylation of hemoglobin is described), chemically reacted and modified hemoglobin of humans, pigs, and cattle, are suitable as hemoglobin starting material. Human and, in particular, porcine hemoglobin is preferred. The hemoglobin can be de-oxygenated (if necessary, also carbonylated), in known manner, if necessary.

Cross-linking of monomeric, untreated hemoglobin, or hemoglobin linked with effectors, is known and described in the literature in many instances, with the following listed as examples:

U.S. Pat. Nos. 4,001,200 and 4,001,401 relate to cross-linked hemoglobins as well as to their use as blood substitutes and plasma expanders. The molecular weights (molar masses) of these cross-linked hemoglobins range from 65,000 to 1,000,000 g/mol. They can be produced by means of a large number of linking agents mentioned, such as, for example, divinyl sulfone, epichlorohydrin, butadiene diepoxide, hexamethylene diisocyanate, the dialdehydes glyoxal and glutardialdehyde, as well as the diimidoesters dimethyl suberimidate, dimethyl malonimidate, and dimethyl adipimidate.

The patent DE 24 49 885 relates (among other things) also to cross-linked hemoglobins, which can be produced by means of the reaction of non-cross-linked hemoglobins with various dialdehydes, for example malondialdehyde, succcindialdehyde, glutardialdehyde, adipindialdehyde, and suberdialdehyde.

U.S. Pat. No. 4,857,636 describes the production of various hemoglobins cross-linked by means of the reaction of hemoglobin with various dialdehydes and polyaldehydes, for example simple ones like glutardialdehyde and glyoxal, but also with structurally more complex ones, which are formed by means of oxidative ring opening of the cyclic half-acetal and half-ketal structures of the sugar molecules to yield monosaccharides and oligosaccharides as well as their derivatives.

U.S. Pat. No. 5,439,882 deals with cross-linked hemoglobins, which are produced by a reaction with the dialdehydes o-adenosine and o-ATP, formed by ring-opening oxidation of ribose into adenosine and in adenosine triphosphate. The cross-linked hemoglobins possess molecular weights of 65,000 to 390,000 g/mol.

The patent EP 0 201 618 relates to a method for producing soluble hemoglobin polymers with an extremely high molecular weight, so-called hyperpolymers (molecular weight up to 15,000,000 g/mol) from highly concentrated solutions of monomeric hemoglobins.

The methods described above are incorporated into the above.

Preferably, bifunctional cross-linking agents are selected for cross-linking the hemoglobins, e.g. butane diepoxide, divinyl sulfone, a diisocyanate, particularly hexamethylene diisocyanate, cyclohexyl diisocyanate, and 2,5-diisocyanate benzene sulfonic acid, a di-N-hydroxy succinimidyl ester, a diimido ester, or a dialdehyde, particularly glyoxal, glycol aldehyde, which reacts analogously, or glutardialdehyde. Glutardialdehyde is preferred.

Cross-linked, oligomeric, polymeric, or hyperpolymeric hemoglobins obtained by the method of the state of the art described above, with molecular weights of about 50,000 to 15,000,000 g/mol and more, particularly of about 50,000 to 10,000,000 g/mol, are considered to be cross-linked hemoglobins pursuant to the invention.

These can be used directly for linking of polyalkylene oxides pursuant to the invention, whereby cross-linked hemoglobins linked with polyalkylene oxide are then formed. Alternatively, the inventive hemoglobins are produced from (non-cross-linked) hemoglobins linked with polyalkylene oxide, by means of reaction with a cross-linking agent according to a known method, for example as described in one of the patents mentioned above. The possible methods of procedure are explained in greater detail below.

It is very particularly preferred if cross-linking takes place with glutardialdehyde, as described, for example, in P ötzschke, H., and Barnikol, W. (1992), *Biomaterials, Artificial Cells, and Immobilization Biotechnology* 20: 287–291, or in the following examples.

With reference to monomeric hemoglobin, in each instance, molar ratios of the cross-linking agents used, particularly of the bifunctional cross-linking agents, of 3 to 60 times, preferably 6 to 35 times, are preferred. With reference to glutardialdehyde, a molar excess of glutardialdehyde that is between 7 and 10 times is preferably used. Chemically unstable links, particularly Schiff's bases, which are formed during the reaction of functional aldehyde groups with amino groups of the hemoglobins, are reductively stabilized in known manner, by means of reaction with suitable reduction agents, such as sodium boron hydride, in a sufficient molar excess, with reference to monomeric hemoglobin, in each instance, preferably 2 to 100 times, particularly preferably 5 to 20 times, under suitable, known conditions.

Many covalent links of polyalkylene oxides to proteins, particularly also to (non-cross-linked) hemoglobins, are known and described in the literature (the state of the art is comprehensively described in: Harris, J. M. (ed.): *Poly (Ethylene Glycol) Chemistry: Biotechnical and Biomedical Applications*, Plenum, N.Y. and others 1992). In the case of very many of these methods, linking of the polyalkylene oxide takes place by way of a molecular bridge ("spacer"), which is created by a bifunctional cross-linking agent, for example. Strictly speaking, in other words, in these cases a linking product of a polyalkylene oxide is linked to the protein with a linking reagent.

For covalent linking of the polyalkylene oxides, those derivatives of the polyalkylene oxides that contain a cross-linking agent with a functional group already covalently bound, which result in a direct chemical reaction with amino, alcohol, or sulfhydryl groups of the hemoglobins, forming covalent links of the polyalkylene oxides, for example polyalkylene oxides with reactive N-hydroxy succinimidyl ester, epoxy (glycidyl ether), aldehyde, isocyanate, vinyl sulfone, iodo-acetamide, imidazolyl formate, tresylate groups, among others, are preferred. Many such monofunctionally activated polyethylene glycols are commercially available, such as the aforementioned, specifically with molecular weights between about 500 and 5,000 g/mol.

Pursuant to the invention, derivatives of a polyalkylene oxide, particularly selected from among polyethylene oxide, polypropylene oxide, or their copolymers, are preferably used. Linking products of polyalkylene oxide, particularly the aforementioned, with a molecule that masks a terminal hydroxy group, particularly an ether, ester, ester amide with a short-chain ($C_1$–$C_5$) aliphatic organic radical are particularly preferably used. Alternatively, non-active polyalkylene oxide can first be chemically activated in any other suitable manner, or, if necessary after any additional derivatization that might be required, linked with the hemoglobin by means of chemical linking agents, for example by means of chemical reaction with bromocyan, a carbodiimide such as 1-ethyl-3-(3-diomethylaminopropyl) carbodiimide or N,N'-dicyclohexyl carbodiimide, cyanuric chloride (polyethylene glycols activated with this substance, 4,6-dichloro-s-triazine-polyethylene glycols, are also commercially available), or other known linking agents such as 2,2'-dichlorobenzidine, p,p'-difluoro-m,m'-dinitrodiphenyl sulfone, 2,4-dichloronitrobenzene, and others (overview in: Harris, J. M. (ed.): *Poly (Ethylene Glycol) Chemistry: Biotechnical and Biomedical Applications*, Plenum, N.Y. and others 1992).

Polyethylene oxides (polyethylene glycols) polypropylene oxides (polypropylene glycols), as well as copolymers (mixed polymers) of ethylene oxide and propylene oxide, particularly, as mentioned, certain derivatives of them, such as compounds that mask a hydroxy group, for example (mono) ethers with a short-chain alcohol, preferably with 1 to 5 carbon atoms, such as monomethyl ether, monopropyl ether, etc., (mono) esters with short-chain carboxylic acids, preferably with 1 to 5 carbon atoms, such as monomethyl ester, monomethyl ester (sic), monopropyl ester, etc., and dehydrogenation products with an aliphatic amine with 1 to 5 carbon atoms, such as monomethylamine, monoethylamine, monopropylamine, etc., with the above, are particularly suitable as polyalkylene oxides. Polyethylene glycols and their stated derivatives are particularly preferred.

The molecular weight of the polyalkylene oxides used is preferably between 200 and 5,000 g/mol, particularly between 500 and 2,000 g/mol.

These are preferably used in an amount of 1 to 40, particularly 4 to 15 moles per mole of hemoglobin.

As already mentioned, linking polyalkylene oxides to proteins (e.g. U.S. Pat. No. 4,179,337 (1979): "Non-immunogenic Polypeptides"), specifically also to hemoglobins, namely also to artificial oxygen carriers on the basis of modified hemoglobins, is already known (U.S. Pat. No. 5,478,805 (1995): "Fractionation of Polyalkylene Oxide-Conjugated Hemoglobin Solution," U.S. Pat. No. 5,386,014 (1995): "Chemically Modified Hemoglobin as an Effective, Stable, Non-immunogenic Red Blood Cell Substitute," EP-A 0 206 448 (1986): "Hemoglobin Combined with a Poly (Alkylene Oxide)," EP-A 0 067 029 (1982): "Oxygen Carrier"). The content of these references is therefore incorporated into the present document. However, linking polyalkylene oxides to artificial oxygen carriers on the basis of modified hemoglobins were never carried out on a cross-linked hemoglobin, according to the literature, and always served to reach completely different types of goals, for example extending the intravasal dwell time, or reducing the immunogenic potency of the artificial oxygen carriers.

The inventive links are produced by the method described above, and depends on the requirements of the chemical reactions selected: Untreated and modified, monomeric and cross-linked hemoglobins are polyelectrolytes and are therefore reacted in aqueous electrolytes with ion concentrations up to 300 mmole/L and preferably of 50 to 170/L with active polyalkylene oxides or linked with polyalkylene oxides by means of activators or linking agents. The reaction temperatures are between 2° and 65° C. and preferably between 3° and 30° C., the proton activity in the solutions, expressed as the pH, is between 5 and 11 and preferably between 6.0 and 10.5, and the reactions times are between a few minutes and up to 24 hours, preferably less than 5 hours and particularly less than 2 hours, depending on the special reaction selected for linking the polyalkylene oxides to the corresponding hemoglobins, and also on the temperature, the pH, the ion concentration, etc.

The hemoglobin, which has not yet been cross-linked, or the cross-linked hemoglobin can therefore be linked with polyalkylene oxide using the known methods described above, for example, by direct combination using a condensation agent such as bromocyan, or by using a cross-linking reagent, such as cyanuric chloride, for example (see DE-OS 30 26 398), or by means of reacting with an activated polyalkylene oxide, for example an N-hydroxysuccinimidyl ester of a polyalkylene oxide derivative. In this manner, at least 1, particularly 1 to 40, and preferably 4 to 15 molecules of the polyalkylene oxide used pursuant to the invention are linked per molecule of monomeric hemoglobin.

As examples, the following methods can be used for linking the polyalkylene oxides, whereby their structural integrity is maintained:

(1) (Non-activated) polyethylene glycol is reacted with 2 to 5 times the molar amount, preferably 3 times the molar amount of bromocyan, at a pH of 9 to 10. The remaining bromocyan is removed from the reaction product by means of gel filtration, dialysis, etc., and the product is then reacted with a required molar amount, e.g. 0.1 to 0.002 times, preferably 0.02 to 0.01 times, of hemoglobin, at pH 7 to 9, preferably 7.5 to 8, in an aqueous solution (see DE-OS 3 026 398);

(2) Polyethylene glycol is added to benzene containing an excess of sodium carbonate, and then reacted with 2 to 5 times the molar amount, preferably 3 to 4 times the molar amount, of cyanuric acid chloride. The reaction product, polyethylene glycol-4,6-dichloro-s-triazine, is separated and reacted with the desired amount, e.g. 1 to 0.002 mole, preferably 0.1 to 0.01 mole, per mole of the aforementioned reaction product, of hemoglobin in a buffer solution with a pH of 8 to 9.5 (see DE-OS 30 26 398);

(3) Activated polyalkylene oxide, for example an N-hydroxysuccinimidyl ester of a polyalkylene oxide, is added to an aqueous solution of a hemoglobin to be linked with the polyalkylene oxide, at a pH of 7 and 10, in a 1 to 40-fold molar excess, relative to the monomeric hemoglobin, and allowed to react.

The methods described above can also be used with other polymers used pursuant to the invention.

The polyalkylene oxides can also be linked chemically to the artificial oxygen carriers of cross-linked hemoglobins at three times different in the course of the production of the inventive hemoglobin derivatives:

i) In the first case, the polyalkylene oxide is bound to the highly pure, untreated or modified hemoglobins (hemoglobin monomers), subsequently cross-linking of the hemoglobins takes place with a cross-linking agent, particularly a bifunctional one.

ii) In the second case, polyalkylene oxide derivatives are coupled to the cross-linked monomer, which has already been synthesized, i.e. subsequent to the reaction of the highly pure, untreated or effector-modified hemoglobin monomers with a bifunctional cross-linking agent.

iii) Finally, in the third case, polyalkylene oxide derivatives can be linked covalently to the hemoglobin monomers before they are cross-linked as well as, additionally, also afterwards, in the further course of the synthesis, to the cross-linked hemoglobin.

The hemoglobin derivative obtained pursuant to the invention can be purified using known, conventional methods, e.g. by means of centrifugation, clear filtration, ultrafiltration or preparative chromatography, such as volume exclusion chromatography, for example on Sephadex G-25 gel or as described in the aforementioned references, or EP-A 0 854 151, EP-A 95 107 280, or in Curling, J. M.: Methods of Plasma Protein Fractionation, Academic Press, London, 1980.

Preferably, monomeric hemoglobin, preferably in the de-oxygenated state, is first cross-linked in an aqueous electrolyte (containing $NaHCO_3$ or NaCl or sodium lactate or several of these, for example), for example using bifunctional cross-linking agents such as butane diepoxide, divinyl sulfone, a diisocyanate, particularly hexamethylene diisocyanate, cyclohexyl diisocyanate, and 2,5-diisocyanateobenzene sulfonic acid, a di-N-hydroxysuccinimidyl ester, a diimido ester, or a dialdehyde, particularly glyoxal, glycol aldehyde, which reacts analogously, and particularly preferably glutardialdehyde, for example in a 3 to 60 times, preferably 6 to 35 times molar excess with reference to monomeric hemoglobin, particularly a 7 to 10 times excess in the case of glutardialdehyde. Excess reactants can be removed in usual manner, by means of suitable additives, e.g. by adding sodium cyanoboron hydride or sodium boron hydride in the case of the dialdehydes (such ad glutardialdehyde, for example), e.g. in a 2 to 100 times, particularly 5 to 20 times molar excess, again with reference to the monomeric hemoglobin.

The cross-linked hemoglobin obtained in solution can then be linked directly with one of the polyalkylene oxides indicated above, for example a polyethylene glycol, a polypropylene glycol, or a copolymerizate of ethylene oxide and propylene oxide or one of the aforementioned derivatives of this, particularly an activated polyethylene glycol such as methoxy-polyethylene glycol-N-hydroxysuccinimidyl propionate (mPEG-SPA), as described. For this purpose, the polyalkylene oxide is used in excess, e.g. in a 1 to 40 times, particularly preferably 4 to 15 times molar ratio with reference to monomeric hemoglobin. The remaining excess can be removed again or inactivated in known manner, e.g. by means of reaction with excess lysine. The polyalkylene oxides have a molar mass of 200 to 5,000, particularly 500 to 2,000 g/mol.

The solution obtained in this way can then be purified in a suitable, known manner, for example chromatographically (e.g. by means of preparative volume exclusion chromatography), by means of centrifugation, (clear) filtration, or ultrafiltration, or by means of precipitation, e.g. with polyethylene oxide, and subsequently be processed further to yield a pharmaceutical preparation.

Alternatively, covalent linking of the polyalkylene oxide can first take place as described, and then subsequently, cross-linking can take place as described. Purification and further processing can be carried out as described, without any changes, also with these alternatives.

The electrolyte concentration and therefore also the pH can be adjusted in accordance with the required conditions, in each instance, as described, in known manner.

In this manner, a cross-linked hemoglobin linked with polyalkylene oxide is obtained as the product, which is surprisingly completely compatible with plasma even under extreme physiological conditions. In this connection, the compatibility is independent of the type and the molecular weight of the hemoglobin, of the cross-linking agent used, of effectors, or of the type of polyalkylene oxide used.

This could not be expected, in view of the state of the art, since there, merely an improved dwell time and a lower immunogenicity, respectively, were achieved in vivo, both by covalent linking of polyalkylene oxides and by cross-linking, but plasma compatibility was not achieved.

The surprising advantages of the inventive hemoglobin derivative can be summarized as follows:

1. Polyalkylene oxide covalently linked to cross-linked hemoglobin results in oxygen carriers that are compatible with plasma. In this connection, the plasma compatibility of these cross-linked hemoglobins is not dependent on the hemoglobin used, in the molecule size of the cross-linked hemoglobins, or on the cross-linking agent.

2. Binding the polyalkylene oxides to the cross-linked hemoglobins ensures, even under disadvantageous pH conditions, that no interactions between the plasma proteins and the cross-linked hemoglobins are to be expected, which would result in precipitation of the cross-linked hemoglobins or of plasma proteins.

3. The modification of cross-linked hemoglobins with polyalkylene oxide allows intravasal use of cross-linked hemoglobins with a high degree of multimerization (hemoglobin polymers)—without such binding, only an application of oligomers would be possible, in order to avoid precipitation phenomena or other interactions, for example with proteins, but also with the blood cells in the plasma. Therefore, additional areas of application in the sector of chromic oxygen deficiency states are opened up to these hemoglobin polymers, aside from their use as a substitute for lost blood volume. Because of their great molecular size, they can be given to a patient as an additional oxygen carrier, as an additive that transports oxygen.

4. In addition, binding of polyalkylene oxides leads to the expectation of an increased vascular residence time, as well as of a reduced immunogenicity.

In this regard, the inventive hemoglobin derivatives can be used as such, or in the form of suitable, e.g. pharmaceutical preparations, as an artificial oxygen carrier intravasally, as a pharmaceutical agent or for biomedical purposes, as a blood substitute for treatment of a blood volume deficiency, as an additive to blood for the treatment of pathogenic oxygen deficiency states, or as a nutrient solution, in the human or animal organism, in organs, or in biotechnical applications. For the production of the products to be administered, the inventive hemoglobin derivatives are dissolved in suitable media, such as infusion solutions, for example in aqueous saline or glucose solution, preferably in concentrations that are isotonic in the blood plasma.

Particularly preferred embodiments of the invention will be explained in greater detail below, first by means of a general method for producing the cross-linked hemoglobins linked with polyalkylene oxides:

1. Purified porcine, human, or bovine hemoglobin with a concentration between 10 and 420 g/L, preferably between 150 and 400 g/L, is dissolved in an aqueous sodium hydrogen carbonate solution, which has a concentration between 10 and 150 mmol/L, preferably of between 40 and 60 mmol/L. De-oxygenation of the hemoglobin takes place by stirring this hemoglobin under a stream of pure nitrogen, at a temperature ranging from 2° to 42° C. and preferably from 3° to 25° C. The pH of the solution is adjusted to a value between 6 and 9 and preferably between 6.5 and 7, using lactic acid or sodium hydroxide solution (having a concentration between 0.1 and 1 mol/L).

2. At the pH adjusted in this way, the reaction of the hemoglobin with a bifunctional cross-linking agent, selected from among butane diepoxide, divinyl sulfone, a diisocyanate, particularly hexamethylene diisocyanate, cyclohexyl diisocyanate, and 2,5-diisocyanate benzene sulfonic acid, a di-N-hydroxysuccinimidyl ester, a diimido ester, or a dialdehyde, particularly glyoxal, glycol aldehyde, which reacts analogously, or glutardialdehyde, with glutardialdehyde being particularly preferred, then takes place. The molar ratio of the cross-linking agent to the monomeric hemoglobin is between 3 and 60, preferably between 6 and 35. After cross-linking with one of the aforementioned dialdehydes, the Schiff's bases that are formed, for example, are reduced with sodium boron hydride, in a molar ratio to the monomeric hemoglobin between 2 and 100, preferably between 5 and 20.

This reduction takes place at a pH between 7.5 and 9, preferably between 7.8 and 8.8, the pH being adjusted this value, as described above (No. 1) with sodium hydroxide solution or lactic acid.

3. After renewed adjustment of the pH to a value between 7 and 9.5 (with sodium hydroxide solution or lactic acid), the cross-linked hemoglobins are linked with one of the aforementioned polyalkylene oxide derivatives, which is added to the reaction mixture in a molar ratio to the monomeric hemoglobin of 1 to 40 and preferably of 4 to 15. The molecular weights of the polyalkylene oxides used are between 200 and 5,000 g/mol, preferably between 500 and 2,000 g/mol. The polyalkylene oxides may already have been activated monofunctionally for the reaction, particularly with amino groups of the hemoglobins, as mentioned above, or, as also described, they may be linked in activated or passive form.

Alternatively, the reaction sequence can also be changed, as already described, and, moreover, monomeric hemoglobin may first be reacted with a polyalkylene oxide and cross-linked afterwards, or finally, polyalkylene oxides may also be linked twice, the reaction sequence then being 1-3-2-3.

The invention will be explained in greater detail by the following examples. In this connection, FIGS. 1 to 6 show the following:

FIG. 1:

A mass-weighted distribution of the molecular sizes and weights (M) of the glutardialdehyde porcine hemoglobin polymer of Example 1, represented as a volume exclusion chromatogram (obtained with Sepharyl S-400 HR gel, Pharmacia, Freiburg, Germany). $E_{425nm}$ is the extinction in the chromatographic eluate at 425 nm, $V_E$ is the elution volume, Vitamin $B_{12}$ serves as the reference substance (internal standard).

FIG. 2:

Results of the in vitro compatibility test of a mixture of the porcine hemoglobin polymers from Example 1 with human plasma (isovolemic mixture), represented as a change in the relative hemoglobin concentrations as a function of the pH after acidification with lactic acid ●: porcine hemoglobin polymers (without covalently linked polyalkylene oxide), ■: porcine hemoglobin polymers with covalently bonded PEG-1000, ♦: porcine hemoglobin polymers with covalently bonded PEG-2000.

FIG. 3:

A mass-weighted distribution of the molecule sizes and molecular weights (M) of the fractionated glutardialdehyde human hemoglobin polymer of Example 2, represented as a volume exclusion chromatogram (obtained with Sepharyl S-400 HR gel, Pharmacia, Freiburg, Germany). $E_{425nm}$ is the extinction in the chromatography eluate at 425 nm, $V_E$ is the elution volume, Vitamin $B_{12}$ serves as the reference substance (internal standard).

FIG. 4:

Results of the in vitro compatibility test of a mixture of the fractionated human hemoglobin polymers from Example 2 with human plasma (isovolemic mixture), represented as a change in the relative hemoglobin concentrations as a function of the pH after acidification with lactic acid ●: human hemoglobin polymers (without covalently linked polyalkylene oxide), ■: human hemoglobin polymers with covalently bonded PEG-1000.

FIG. 5:

A mass-weighted distribution of the molecule sizes and molecular weights (M) of the fractionated glutardialdehyde bovine hemoglobin polymer of Example 3, represented as a volume exclusion chromatogram (obtained with Sepharyl S-400 HR gel, Pharmacia, Freiburg, Germany). $E_{425nm}$ is the extinction in the chromatography eluate at 425 nm, $V_E$ is the elution volume, Vitamin $B_{12}$ serves as the reference substance (internal standard).

FIG. 6:

Results of the in vitro compatibility test of a mixture of the fractionated bovine hemoglobin polymers from Example 3 with human plasma (isovolemic mixture), represented as a change in the relative hemoglobin concentrations as a function of the pH after acidification with lactic acid ■: bovine hemoglobin polymers (without covalently linked polyalkylene oxide), ●: bovine hemoglobin polymers with covalently bonded PEG-1000.

EXAMPLE 1

Covalent Linking of Monofunctional N-hydroxy-succinimidyl Propionate Polyethylene Glycol (mPEG-SPA) with Molar Masses of 1,000 g/mol (mPEG-SPA) and 2,000 g/mol (mPEG-SPA-2000) to Covalently Cross-linked Porcine Hemoglobin The cross-linked porcine hemoglobins was synthesized (slightly modified) by the method of Dinkelmann, S. ("Präparation und in vitro Charakterisierung eines künstlichen Sauerstoffträgers auf der Basis von Schweinehämoglobin und seine Evaluierung im Kleintier" (Preparation and in vitro characterization of an artificial oxygen carrier on the basis of porcine hemoglobin and its evaluation in small animals), *Dissertation, Department of Medicine, Johannes Gutenberg University*, Mainz, 1997, see also Pötzschke, H., et al., *Art. Cells, Blood Subst. and Immob. Biotechn.* 25 (1997), 527–540) and Domack, U. ("Entwicklung und in vivo Evaluation eines künstlichen Sauerstoffträgers auf Basis von Rinderhämoglobin" (Development and in vivo evaluation of an artificial oxygen carrier on the basis of bovine hemoglobin), *Dissertation, Department of Chemistry, Johannes Gutenberg University*, Mainz, 1997): Highly pure, concentrated, de-oxygenated porcine hemoglobin, dissolved in an aqueous electrolyte with the composition 50 mmol/L $NaHCO_3$ and 100 mmol/L NaCl was reacted with a 14 times molar excess of glutardialdehyde at room temperature. Sodium cyanoboron hydride, added to the (monomeric) hemoglobin in a 10 times molar excess, reduced the Schiff's bases that were formed during cross-linking, and stabilized the covalent cross-linking. The solution of cross-linked hemoglobins that was obtained was divided into three parts (A, B, and C) and further processing continued in different ways.

Part A remained unchanged, determination of the molecular weight distribution (according to Pötzschke, H., et al. (1996): "Vernetzte globuläre Proteine—eine neue Klasse halb-synthetischer polymerer Moleküle: Charakterisierung ihrer Struktur in Lösung am Beispiel hyperpolymeren Hämoglobins und Myoglobins mittels Volumenausschluss-Chromatographie, Viskosimetrie, Osmometrie und Lichtstreuung" (Cross-linked globular proteins—a new class of semi-synthetic polymer molecules: Characterization of their structure in solution, using the example of hyperpolymer hemoglobin and myoglobin by means of volume exclusion chromatography, viscosimetry, osmometry, and light scattering), *Macromolecular Chemistry and Physics* 197, 1419–1437, as well as Plötzschke, H., et al. (1996): "Ein neuartiges Verfahren zur Bestimmung Molarer Massen breit verteilter Polymerer mit Hilfe der Gel-Chromatographie und der Viskosimetrie am Beispiel Hämoglobin-Hyperpolymerer" (A new kind of method for the determination of molar masses of broadly distributed polymers using gel chromatography and viscosimetry, using the example of hemoglobin hyperpolymers), *Macromolecular Chemistry and Physics* 197, 3229–3250) using volume exclusion chromatography with Sepharyl S-400 HR gel (Pharmacia Biotech, Freiburg, Germany) resulted in a modal value of the molecular weight distribution of 530 kg/mol for the cross-linked porcine hemoglobin (FIG. 1 shows a chromatogram).

The polymers of part B were covalently linked with monofunctionally active mPEG-SPA-1000 (Shearwater Polymers Europe, Enschede, Netherlands): First, sodium hydrogen carbonate was added to the solution of the cross-linked hemoglobins, as a solid, up to a final concentration of 150 mmol/L, subsequently, mPEG-SPA-1000 was added in a 12 times molar excess (with reference to the hemoglobin monomers), also as a solid. After a reaction time of one hour, lysine was added in a 60 times molar excess (with reference to hemoglobin) and reacted with any remaining active mPEG-SPA-1000 molecules.

Part C: The method of procedure was the same with the solution of cross-linked monomers as described for Part B, but mPEG-SPA-2000 (Shearwater Polymers Europe, Enschede, Netherlands) was used.

Subsequently, the solvent was exchanged in the three solutions A, B, and C (using an ultrafiltration, "Ultraminisette 10 kDa," Pall Gelman Sciences, Rossdorf, Germany, or volume exclusion chromatography using the gel "Sephadex G-15 M," Pharmacia Biotech, Freiburg, Germany), to produce a solution in an aqueous electrolyte (StLg) with the composition: 125 mM NaCl, 4.5 mM KCl, and 3 mM $NaN_3$.

The study of the plasma compatibility of the non-modified (A) porcine hemoglobin as well as that modified with PEG (B and C) took place by means of a standardized in vitro precipitation test (Domack, U. (1997), see above). The hemoglobin solutions were mixed with equal amounts of freshly collected, sterile filtered human plasma and subsequently, up to 20 μL 0.5 molar lactic acid were added to 500 μL of the mixture, in each instance, so that pH values in a range between 7.4 and 6.8 resulted for each hemoglobin derivative to be studied. After an incubation period of 30 minutes at room temperature, and centrifugation of the samples, the hemoglobin content was determined (modified cyan hemoglobin method according to Drabkin: "Hämoglobin-Farbtest (hemoglobin color test) MRP 3," Boehringer Mannheim, Germany), as was the related pH value (blood gas analyzer "ABL 5," Radiometer, Willich, Germany), in the top fraction.

Figure 2:
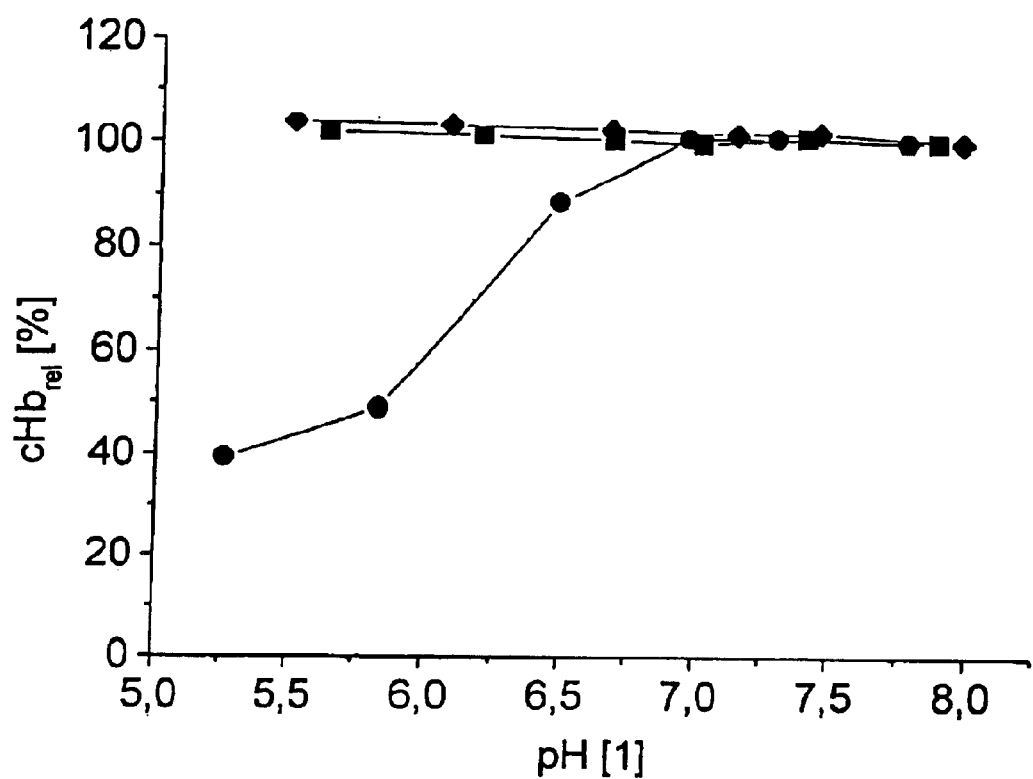
Figure 3:
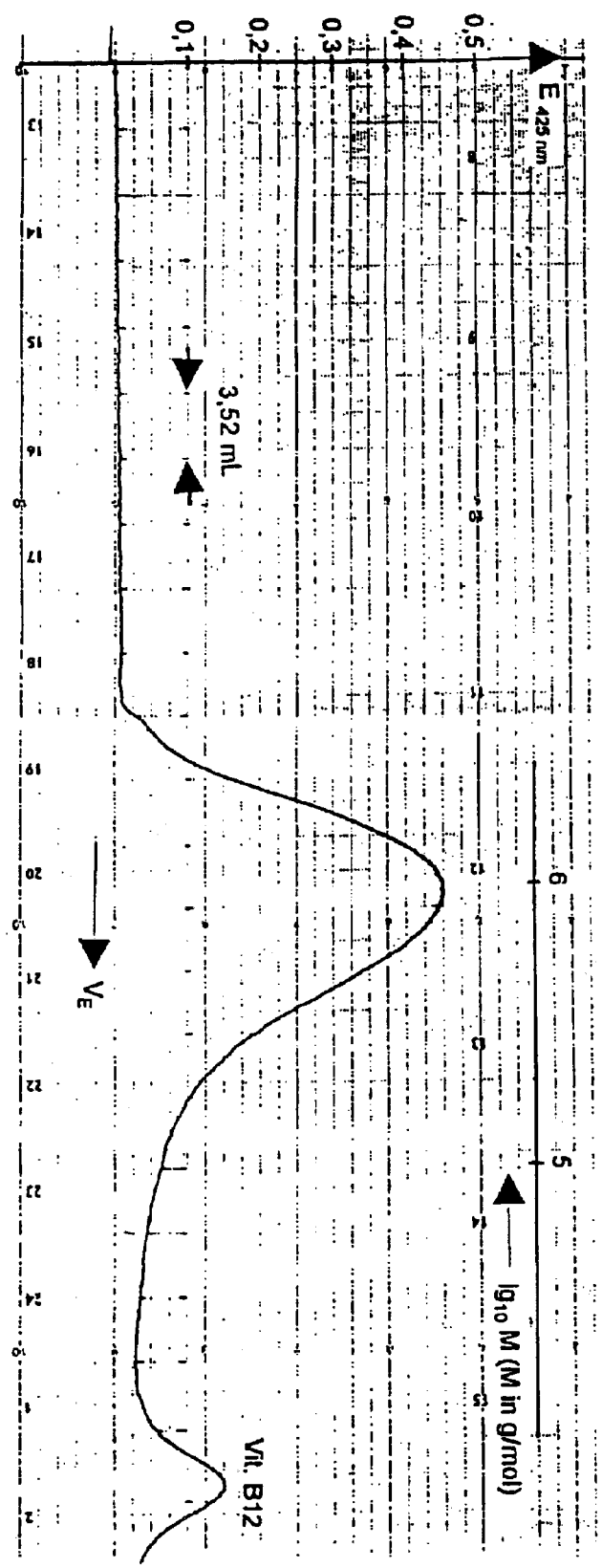

FIG. 2 shows the relative hemoglobin concentrations (with reference to the starting hemoglobin concentration before adding the lactic acid) as a function of the pH of the hemoglobin-plasma mixture, reductions result from the precipitation of non-compatible portions. For pH values less than 7.0, red precipitates were observed for the A sample (non-modified porcine hemoglobin polymer), which represent a reduction in the hemoglobin concentration. For this cross-linked porcine hemoglobin, such incompatibility must be expected in vivo, as well, in the pH interval from 7.4 to 6.8. In contrast, no precipitates were observed in the cross-linked hemoglobins B and C modified with PEG, in the physiologically interesting range between the pH values 7.4 and 6.8, and beyond that, even to 5.5, and the hemoglobin content did not decrease.

In the pH range from 7.4 to 6.8, which is physiologically and pathophysiologically interesting, it was therefore possible to achieve protection of the cross-linked porcine hemoglobins as well as of the plasma proteins against precipitates caused by interactions, by means of the covalent binding of both PEG-1000 and PEG-2000 to these hemoglobins.

EXAMPLE 2

Covalent Linking of mPEG-SPA (N-hydroxysuccinimidyl Propionate Polyethylene Glycol) with a Molar Mass of 1,000 g/mol to Covalently Crosslinked Human Hemoglobin The synthesis of the human hemoglobin cross-linked with glutardialdehyde took place as in Example 1, but using highly pure, concentrated human hemoglobin and using a 16 times molar excess of the cross-linking agent. Polymers were obtained by fractionation of the solution of the cross-linking products using preparative volume exclusion chromatography (according to EP-A 95 10 72 80.0: "Verfahren zur Herstellung molekular-einheitlicher hyperpolymerer Hamoglobine" (Method for the production of molecular-uniform hyperpolymer hemoglobins) with Sepharyl S-300 HR gel, Pharmacia Biotech, Freiburg, Germany) (here as the first eluted 57 mass-% of the cross-linked hemoglobin).

The cross-linked hemoglobins were divided up into parts A and B. Hemoglobin A (see FIG. 3) proved to be predominantly polymer hemoglobin with a modal value of the molecular weight distribution of 950 kg/mol (see Example 1). Covalent binding of monofunctionally active mPEG-SPA-1000 took place analogous to the method of procedure described in Example 1 for cross-linked porcine hemoglobin. After the addition of sodium hydrogen carbonate (up to 150 mM) to the solution of the polymers, a 12 times molar excess mPEG-SPA-1000 was able to react with the hemoglobin monomers. Subsequent to a reaction time of one hour, lysine was added in a 60 times molar excess, to "capture" any remaining active molecules of the mPEG-SPA-1000. As a preparation for the in vitro biocompatibility test, re-washing (solvent exchange) of solutions A and B in the aqueous electrolytes (StLg" took place (completely analogous as described in Example 1).

Figure 4:
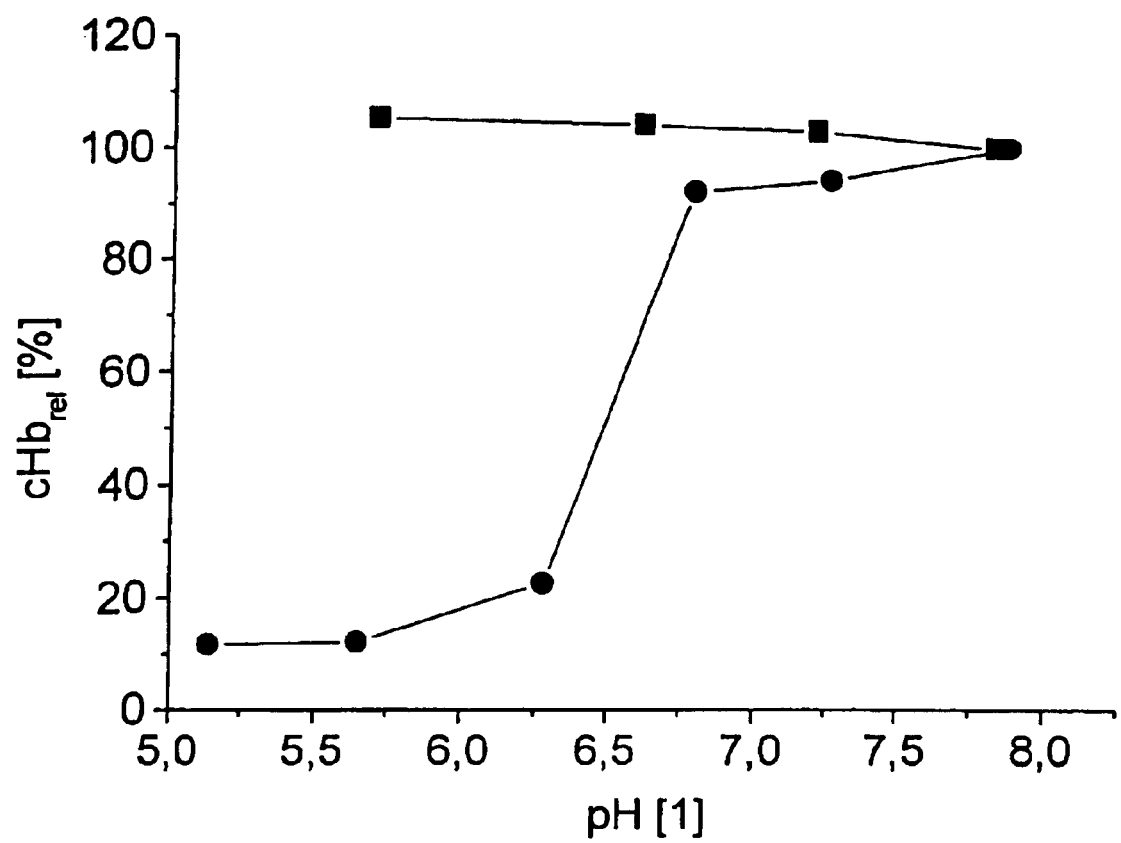

The precipitation test (the results are shown in FIG. 4) resulted in red precipitates for the cross-linked hemoglobins A for the entire studied pH interval of 7.9 to 5.1. For example, in the case of a simulation of acidosis with a pH of 6.8, approximately 8% of the hemoglobin polymers precipitated. At a pH of 5.7, a maximum of precipitates is reached. Only modification with mPEG-1000 prevents the occurrence of hemoglobin precipitates far into the acidic range, up to a pH of 5.7.

EXAMPLE 3

Covalent Linking of mPEG-SPA-1000 to Crosslinked Bovine Hemoglobin

Cross-linked bovine hemoglobin was produced by cross-linking concentrated bovine hemoglobin of high purity with a 14-fold molar excess of glutardialdehyde, as in Example 1, molecularly fractionating the synthesis products, linking the mPEG-SPA-1000 and the preparative preparation for the in vitro precipitation titration of Example 2.

Figure 5:
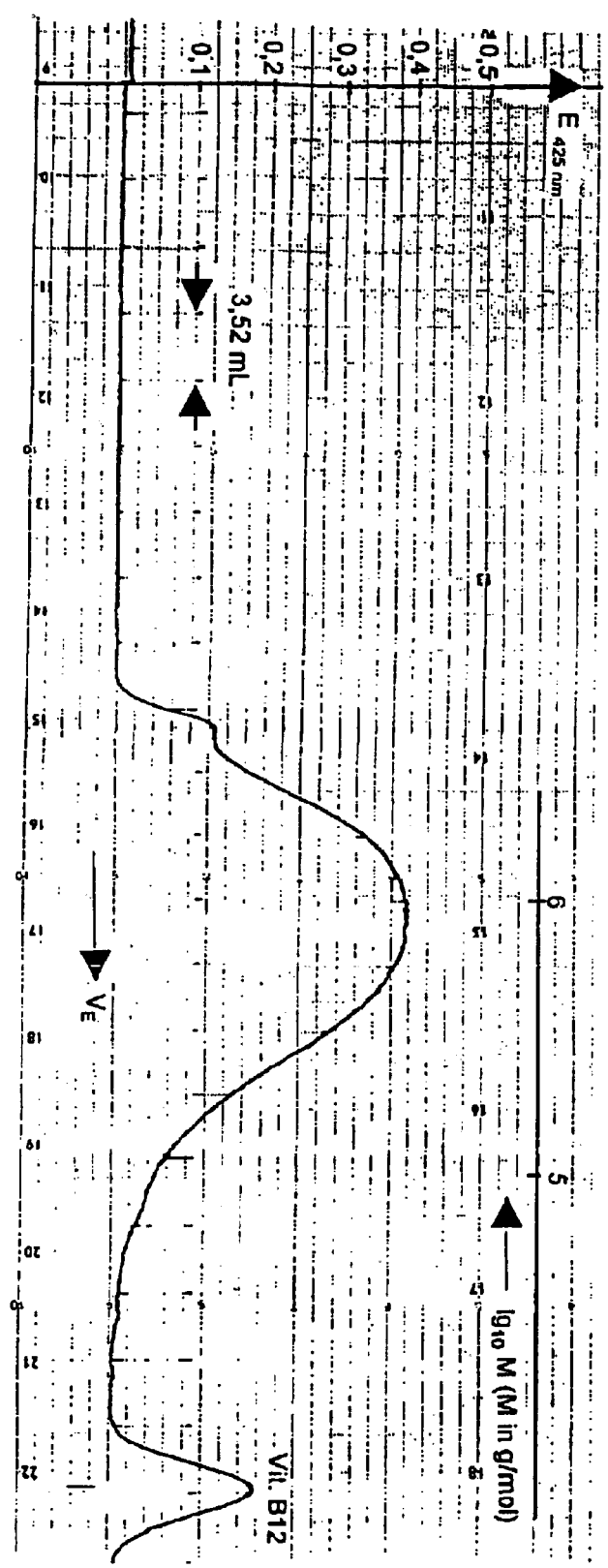

A molecular weight distribution of the non-modified hemoglobin polymer is shown in FIG. 5, namely an eluogram of a volume exclusion chromatography (using the gel "Sepharyl S-400 HR," Pharmacia Biotech, Freiburg, Germany), the modal value of the molecular weight distribution is 810 kg/mol here.

Figure 6:
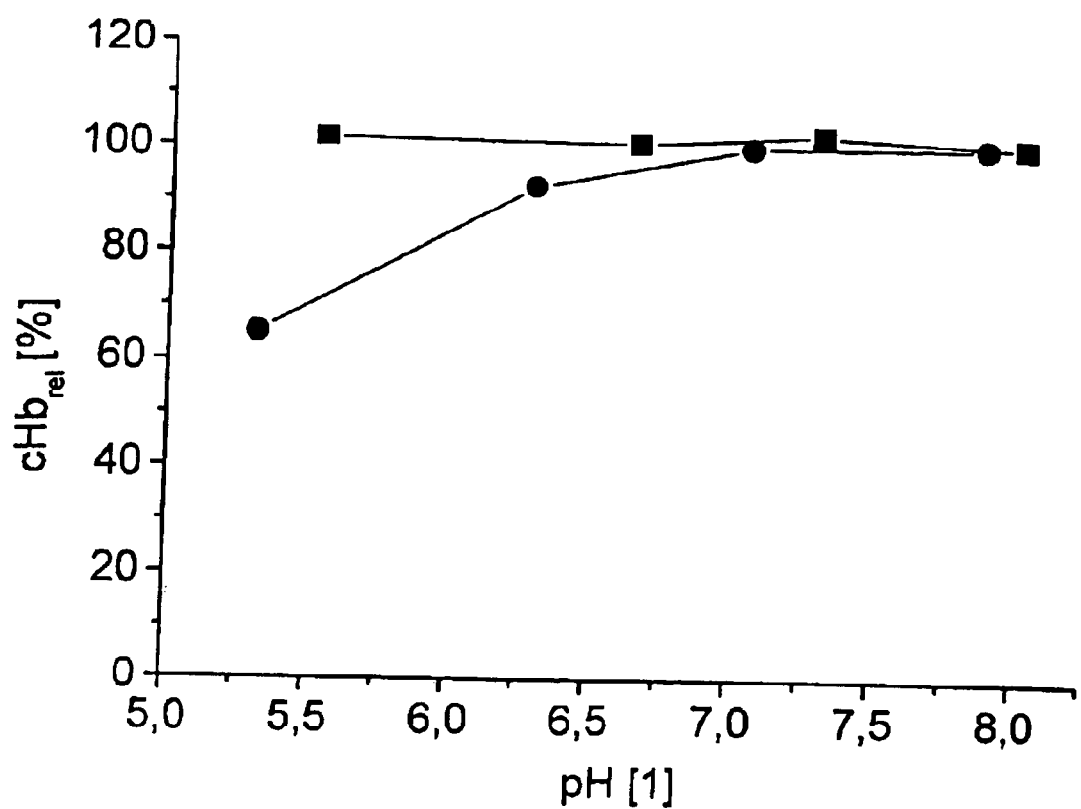

In the in vitro precipitation test (the results are shown in FIG. 6), hemoglobin polymer precipitates were observed for the fractionated, non-modified bovine hemoglobin polymer in the pH interval of 7.9 to 5.3. The sample containers of the bovine hemoglobin polymers modified with PEG, with pH values between 8.0 and 6.7, on the other hand, did not contain any centrifugates after centrifugation.

By covalently linking of PEG-1000, the plasma compatibility of the cross-linked bovine hemoglobin is increased to such an extent, that parenteral administration is possible, since precipitates do not have to be expected in vivo.

What is claimed is:

1. Hemoglobin derivative compatible with human and non-human animal plasma, comprising hemoglobin crosslinked by means of a crosslinker for proteins and a polyalkylene oxide covalently linked to the hemoglobin, with polyalkylene oxides being excluded as crosslinker and no reaction with diaspirin taking place, said crosslinker being a bifunctional crosslinker for proteins, selected from the group consisting of butane diepoxide, divinyl sulfone, a diisocyanate, a di-N-hydroxysuccinimidyl ester, a diimido ester and a dialdehyde.

2. Hemoglobin derivative compatible with plasma according to claim 1, wherein the hemoglobin is of human origin, from the cow or from the pig.

3. Hemoglobin derivative compatible with plasma according to claim 1, wherein a derivative of a polyalkylene oxide, selected from polyethylene oxide, polypropylene oxide or copolymers of ethylene oxide and propylene oxide is linked to the hemoglobin.

4. Hemoglobin derivative according to claim 3, wherein between 1 and 40 molecules of polyalkylene oxide are linked per molecule of the hemoglobin monomer.

5. Hemoglobin derivative according to claim 1, wherein the hemoglobin is crosslinked by means of glutaric dialdehyde.

6. Hemoglobin derivative according to claim 1, wherein the crosslinked hemoglobin has molecular weights up to 10,000,000 g/mol.

7. Method for the preparation of hemoglobin derivatives as synthetic oxygen carriers which are compatible with human and non-human animal blood plasma, comprising crosslinking the hemoglobin with a crosslinker for proteins and covalently linking a polyalkylene oxide to the hemoglobin, the crosslinked hemoglobin having a molecular weight from 50,000 to 10,000,000 g/mol, polyalkylene oxides as crosslinkers being excluded and no reaction with diaspirin takes place.

8. Method according to claim 7, characterized either
   (i) first polyalkylene oxide is covalently linked to hemoglobin and this hemoglobin linked to polyalkylene oxide is then crosslinked, or
   (ii) first the hemoglobin is crosslinked and then polyalkylene oxide is linked covalently to the crosslinked hemoglobin, or
   (iii) first polyalkylene oxide is covalently linked to hemoglobin, this hemoglobin linked to polyalkylene oxide is then crosslinked, and to this hemoglobin linked to polyalkylene oxide and crosslinked, polyalkylene oxide is again covalently linked.

9. Method according to claim 7, wherein the hemoglobins is from humans, cattle or pigs.

10. Method according to claim 7, wherein hemoglobin in an aqueous electrolyte solution is crosslinked with a 3 to 60 times molar excess, with respect to monomeric hemoglobin, of a bifunctional crosslinker for proteins, and covalently linked with a 1 to 40 times molar excess, with respect to monomeric hemoglobin, of a polyalkylene oxide, and then the excess of the reactants is removed and the product is purified.

11. Method according to claim 10, wherein the bifunctional crosslinker for proteins is selected from butane diepoxide, divylsulfone, a diisocyanate, a di-N-hydroxysuccinimidyl ester, a diimido ester and a dialdehyde.

12. Method according to claim 11, wherein the bifunctional crosslinker for proteins is glutaric dialdehyde.

13. Method according to claim 7, wherein a derivative of a polyethylene oxide, polypropylene oxide, or copolymers of ethylene oxide and propylene oxide is used as polyalkylene oxide.

14. Method of using a crosslinked hemoglobin compatible with plasma according to claim 1, for intravascular or biomedical application as an artificial oxygen carriers, said method comprising administering said artificial oxygen carrier to a patient in need thereof.

15. Method according to claim 14, which comprises administering the crosslinked hemoglobin to a patient in need thereof as a substitute for blood, or as an additive to blood, or in a nutrient solution.

16. Hemoglobin derivative according to claim 1, wherein the diisocyanate is hexamethylene diisocyanate, cyclohexyl diisocyanate or 2,5-bisisocyanatobenzenesulfonic acid; or the dialdehyde is glyoxal, glycol aldehydes or glutaric dialdehyde.

17. Method according to claim 11, wherein the diisocyanate is hexamethylene diisocyanate, cyclohexyl diisocyanate or 2,5-bisisocyanatobenzenesulfonic acid; or the dialdehyde is glyoxal, glycol aldehydes or glutaric dialdehyde.

* * * * *